US008891080B2

(12) United States Patent
Khusnatdinov et al.

(10) Patent No.: US 8,891,080 B2
(45) Date of Patent: Nov. 18, 2014

(54) CONTAMINATE DETECTION AND SUBSTRATE CLEANING

(75) Inventors: Niyaz Khusnatdinov, Round Rock, TX (US); Dwayne L. LaBrake, Cedar Park, TX (US)

(73) Assignees: Canon Nanotechnologies, Inc., Austin, TX (US); Molecular Imprints, Inc., Austin, TX (US)

( * ) Notice: Subject to any disclaimer, the term of this patent is extended or adjusted under 35 U.S.C. 154(b) by 291 days.

(21) Appl. No.: 13/178,268

(22) Filed: Jul. 7, 2011

(65) Prior Publication Data

US 2012/0006703 A1    Jan. 12, 2012

Related U.S. Application Data

(60) Provisional application No. 61/362,377, filed on Jul. 8, 2010.

(51) Int. Cl.
| | | |
|---|---|---|
| *G01N 21/00* | (2006.01) | |
| *G01N 21/956* | (2006.01) | |
| *G01N 21/94* | (2006.01) | |
| *G01N 21/47* | (2006.01) | |

(52) U.S. Cl.
CPC .............. *G01N 21/94* (2013.01); *G01N 21/956* (2013.01); *G01N 21/47* (2013.01); *G01N 21/00* (2013.01); *Y10S 977/887* (2013.01)
USPC ................... 356/237.3; 356/237.1; 356/237.2; 356/237.4; 356/237.5; 264/293; 977/887

(58) Field of Classification Search
USPC ............. 264/293; 977/887; 356/237.1, 237.2, 356/237.3, 237.4, 237.5
See application file for complete search history.

(56) References Cited

U.S. PATENT DOCUMENTS

| | | | |
|---|---|---|---|
| 5,805,278 A * | 9/1998 | Danko ....................... | 356/237.1 |
| 6,224,679 B1 | 5/2001 | Sasaki et al. | |
| 6,284,020 B1 | 9/2001 | Mizuno et al. | |
| 6,440,621 B1 | 8/2002 | Sutton et al. | |
| 6,521,007 B1 | 2/2003 | Tanaka et al. | |
| 6,547,953 B2 | 4/2003 | Suzuki et al. | |
| 6,873,087 B1 | 3/2005 | Choi et al. | |
| 6,932,934 B2 | 8/2005 | Choi et al. | |
| 6,936,194 B2 | 8/2005 | Watts | |
| 7,077,992 B2 | 7/2006 | Sreenivasan et al. | |
| 7,157,036 B2 | 1/2007 | Choi et al. | |
| 7,179,396 B2 | 2/2007 | Sreenivasan | |
| 7,396,475 B2 | 7/2008 | Sreenivasan | |
| 8,194,242 B2 * | 6/2012 | Derksen et al. ............. | 356/237.5 |
| 2004/0065252 A1 | 4/2004 | Sreenivasan et al. | |
| 2004/0065976 A1 | 4/2004 | Sreenivasan et al. | |
| 2004/0223883 A1 * | 11/2004 | Choi et al. ................. | 422/82.05 |
| 2005/0187339 A1 | 8/2005 | Xu et al. | |
| 2007/0246850 A1 | 10/2007 | Schumaker | |
| 2007/0264591 A1 * | 11/2007 | Wuister et al. ................ | 430/269 |

(Continued)

FOREIGN PATENT DOCUMENTS

| | | |
|---|---|---|
| KR | 10-2007-0087760 | 8/2007 |
| KR | 10-0794687 | 1/2008 |

*Primary Examiner* — Jeremiah Smith
(74) *Attorney, Agent, or Firm* — Cameron A. King (57) ABSTRACT

Detection of periodically repeating nanovoids is indicative of levels of substrate contamination and may aid in reduction of contaminants on substrates. Systems and methods for detecting nanovoids, in addition to, systems and methods for cleaning and/or maintaining cleanliness of substrates are described.

4 Claims, 7 Drawing Sheets

(56) References Cited

U.S. PATENT DOCUMENTS

2008/0187873 A1* 8/2008 Bandic et al. ............... 430/322
2008/0308971 A1* 12/2008 Liu et al. ..................... 264/293
2011/0151361 A1* 6/2011 Takahashi et al. ............. 430/30
2011/0272382 A1* 11/2011 Owa et al. ..................... 216/37

* cited by examiner

CONTAMINATE DETECTION AND SUBSTRATE CLEANING

CROSS-REFERENCE TO RELATED APPLICATION

The present application claims priority to U.S. Provisional Application No. 61/362,377 filed on Jul. 8, 2010, which is hereby incorporated by reference in its entirety.

BACKGROUND INFORMATION

Nano-fabrication includes the fabrication of very small structures that have features on the order of 100 nanometers or smaller. One application in which nano-fabrication has had a sizeable impact is in the processing of integrated circuits. The semiconductor processing industry continues to strive for larger production yields while increasing the circuits per unit area formed on a substrate; therefore nano-fabrication becomes increasingly important. Nano-fabrication provides greater process control while allowing continued reduction of the minimum feature dimensions of the structures formed. Other areas of development in which nano-fabrication has been employed include biotechnology, optical technology, mechanical systems, and the like.

An exemplary nano-fabrication technique in use today is commonly referred to as imprint lithography. Exemplary imprint lithography processes are described in detail in numerous publications, such as U.S. Patent Publication No. 2004/0065976, U.S. Patent Publication No. 2004/0065252, and U.S. Pat. No. 6,936,194, all of which are hereby incorporated by reference herein.

An imprint lithography technique disclosed in each of the aforementioned U.S. patent publications and patent includes formation of a relief pattern in a formable (polymerizable) layer and transferring a pattern corresponding to the relief pattern into an underlying substrate. The substrate may be coupled to a motion stage to obtain a desired positioning to facilitate the patterning process. The patterning process uses a template spaced apart from the substrate and a formable liquid applied between the template and the substrate. The formable liquid is solidified to form a rigid layer that has a pattern conforming to a shape of the surface of the template that contacts the formable liquid. After solidification, the template is separated from the rigid layer such that the template and the substrate are spaced apart. The substrate and the solidified layer are then subjected to additional processes to transfer a relief image into the substrate that corresponds to the pattern in the solidified layer.

The level of cleanliness of substrates used in imprint lithography is important for quality results. Contamination of substrate surfaces may cause defects in and/or delamination of the formed layer, voids, particulates and the like. Direct analysis of substrate surface contamination, using for example GC-MS and TOF-SIMS techniques, is expensive and time-consuming, and in many cases can be inconclusive.

SUMMARY

Aspects of the present invention include methods for detecting levels of surface contamination of an imprint lithography substrate that are advantageously based on the detection of levels of periodically occurring nanovoids in an imprinted layer formed on the substrate. In one aspect, such a method can include providing a substrate, depositing polymerizable material in a periodic drop pattern on the substrate, contacting the polymerizable material with a planar imprint template, polymerizing the polymerizable material to form an imprint layer on the substrate, and then detecting the presence of defects on the imprint layer. The detected defects are analyzed and the periodically occurring nanovoid defects within the detected defects are identified. The number of periodic nanovoid defects per unit surface area of the substrate correlates to the level of surface contamination of the substrate.

In certain aspects, the detection of substrate defects can use light scattering techniques, and further include generating a scatter map of the substrate. The total number of detected defects can be obtained from the scatter map. In further aspects, the analysis of the detected defects can included performing a Fourier transform (FFT) analysis of the scatter map. The ratio of periodic nanovoid defects to total detected defects can be obtained from the Fourier transform (FFT) analysis based on a ratio of the obtained first and zero order Fourier peak volumes. Multiplying this ratio by the total number of detected defects yields the number of periodic nanovoid defects.

Other aspects of the invention include methods for reducing surface contamination of substrates used in imprint lithography. Such methods can include providing a substrate, cleaning the substrate to remove existing surface contamination from the substrate, and then storing the cleaned substrate in a sealed environment filtered by a chemical filter suitable for removing organic contaminants from air. Exemplary chemical filters include carbon filters. In further aspects, the sealed environment can also be filtered by a high efficiency particle air (HEPA) filter to protect against particulate contaminants. The stored substrates can be uncoated or coated with, for example, an adhesive coating.

Further aspects of the invention include incorporation of such chemical filters in systems for the handling, storing and processing of such substrates. In one aspect, a system is provided having an enclosure containing a cleaning tool for cleaning a substrate, a coating tool for coating the substrate; a storage container for storing the substrate, and an imprint lithography system for imprinting the substrate, one or more inlet openings to the enclosure for providing an airflow to the enclosure, and a chemical filter positioned to filter the airflow provided to the enclosure.

In other aspects, the cleaning tool, coating tool, storage container and an imprint lithography system can each be contained in a separate enclosure, each with separate dedicated inlet opening and chemical filters positioned to separately filter airflow to each enclosure. Again the chemical filters can be carbon filters, and can further be provided in sequence with a high efficiency particle air (HEPA) filters. In yet another aspect, the system can further include one or more airtight sealable portable substrate transfer modules for transferring a substrate between the separate enclosures.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF DRAWINGS

So that features and advantages of the present invention can be understood in detail, a more particular description of embodiments of the invention may be had by reference to the embodiments illustrated in the appended drawings. It is to be noted, however, that the appended drawings only illustrate typical embodiments of the invention, and are therefore not to be considered limiting of its scope, for the invention may admit to other equally effective embodiments.

FIG. 1 illustrates a simplified side view of a lithographic system.

DETAILED DESCRIPTION

Figure 1:
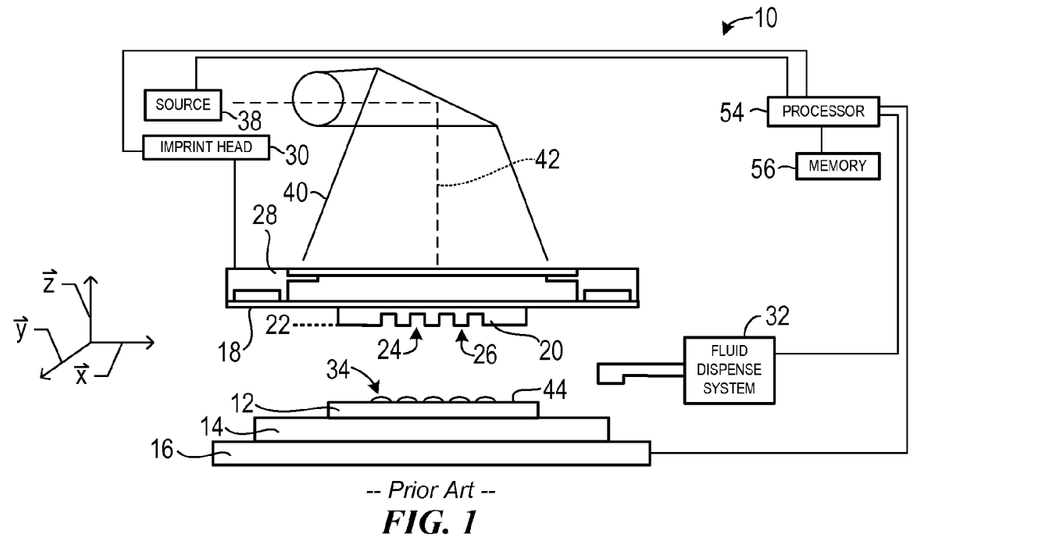

Referring to the figures, and particularly to FIG. 1, illustrated therein is a lithographic system 10 used to form a relief pattern on substrate 12. Substrate 12 may be coupled to substrate chuck 14. As illustrated, substrate chuck 14 is a vacuum chuck. Substrate chuck 14, however, may be any chuck including, but not limited to, vacuum, pin-type, groove-type, electrostatic, electromagnetic, and/or the like. Exemplary chucks are described in U.S. Pat. No. 6,873,087, which is hereby incorporated by reference herein.

Substrate 12 and substrate chuck 14 may be further supported by stage 16. Stage 16 may provide translational and/or rotational motion along the x, y, and z-axes. Stage 16, substrate 12, and substrate chuck 14 may also be positioned on a base (not shown).

Spaced-apart from substrate 12 is template 18. Template 18 may include a body having a first side and a second side with one side having a mesa 20 extending therefrom towards substrate 12. Mesa 20 having a patterning surface 22 thereon. Further, mesa 20 may be referred to as mold 20. Alternatively, template 18 may be formed without mesa 20.

Template 18 and/or mold 20 may be formed from such materials including, but not limited to, fused-silica, quartz, silicon, organic polymers, siloxane polymers, borosilicate glass, fluorocarbon polymers, metal, hardened sapphire, and/or the like. As illustrated, patterning surface 22 comprises features defined by a plurality of spaced-apart recesses 24 and/or protrusions 26, though embodiments of the present invention are not limited to such configurations (e.g., planar surface). Patterning surface 22 may define any original pattern that forms the basis of a pattern to be formed on substrate 12.

Template 18 may be coupled to chuck 28. Chuck 28 may be configured as, but not limited to, vacuum, pin-type, groove-type, electrostatic, electromagnetic, and/or other similar chuck types. Exemplary chucks are further described in U.S. Pat. No. 6,873,087, which is hereby incorporated by reference herein. Further, chuck 28 may be coupled to imprint head 30 such that chuck 28 and/or imprint head 30 may be configured to facilitate movement of template 18.

System 10 may further comprise a fluid dispense system 32. Fluid dispense system 32 may be used to deposit formable material 34 (e.g., polymerizable material) on substrate 12. Formable material 34 may be positioned upon substrate 12 using techniques, such as, drop dispense, spin-coating, dip coating, chemical vapor deposition (CVD), physical vapor deposition (PVD), thin film deposition, thick film deposition, and/or the like. Formable material 34 may be disposed upon substrate 12 before and/or after a desired volume is defined between mold 22 and substrate 12 depending on design considerations. Formable material 34 may be functional nanoparticles having use within the bio-domain, solar cell industry, battery industry, and/or other industries requiring a functional nano-particle. For example, formable material 34 may comprise a monomer mixture as described in U.S. Pat. No. 7,157,036 and U.S. Patent Publication No. 2005/0187339, both of which are herein incorporated by reference. Alternatively, formable material 34 may include, but is not limited to, biomaterials (e.g., PEG), solar cell materials (e.g., N-type, P-type materials), and/or the like.

Figure 2:
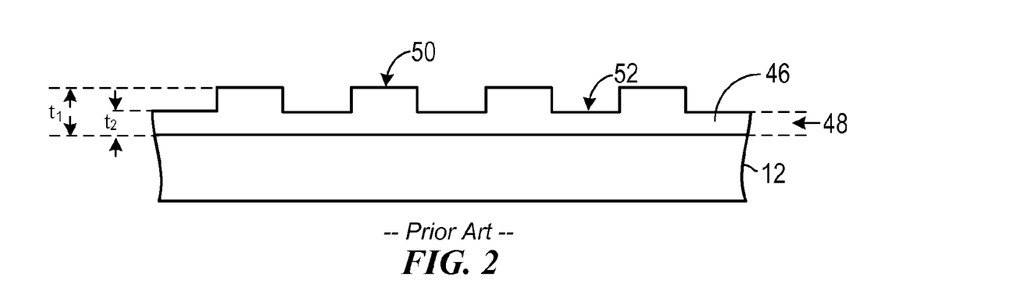
FIG. 2 illustrates a simplified side view of the substrate illustrated in FIG. 1, having a patterned layer thereon.

Referring to FIGS. 1 and 2, system 10 may further comprise energy source 38 coupled to direct energy 40 along path 42. Imprint head 30 and stage 16 may be configured to position template 18 and substrate 12 in superimposition with path 42. System 10 may be regulated by processor 54 in communication with stage 16, imprint head 30, fluid dispense system 32, and/or source 38, and may operate on a computer readable program stored in memory 56.

Either imprint head 30, stage 16, or both vary a distance between mold 20 and substrate 12 to define a desired volume therebetween that is filled by formable material 34. For example, imprint head 30 may apply a force to template 18 such that mold 20 contacts formable material 34. After the desired volume is filled with formable material 34, source 38 produces energy 40, e.g., ultraviolet radiation, causing formable material 34 to solidify and/or cross-link conforming to a shape of surface 44 of substrate 12 and patterning surface 22, defining patterned layer 46 on substrate 12. Patterned layer 46 may comprise a residual layer 48 and a plurality of features shown as protrusions 50 and recessions 52, with protrusions 50 having a thickness $t_1$ and residual layer having a thickness $t_2$.

The above-mentioned system and process may be further employed in imprint lithography processes and systems referred to in U.S. Pat. No. 6,932,934, U.S. Pat. No. 7,077,992, U.S. Pat. No. 7,179,396, and U.S. Pat. No. 7,396,475, all of which are hereby incorporated by reference in their entirety.

Nanovoid Detection

Figure 3:
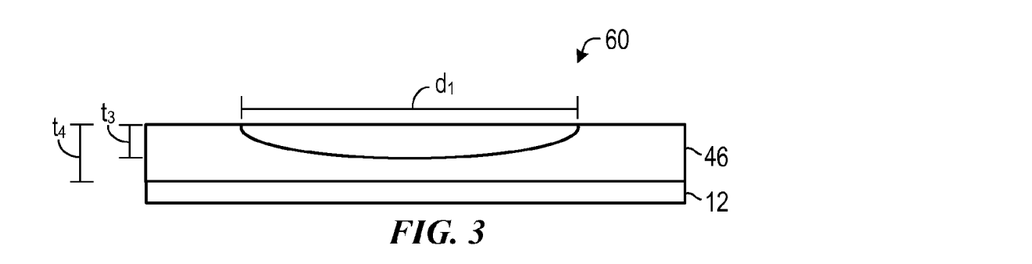
FIG. 3 illustrates a simplified side view of a patterned layer having a nanovoid formed therein.

As noted, contamination of the substrate in imprint lithography may lead to defects in the formed layer, including delamination and/or the presence of voids, particulates, and the like in the formed imprint layer. In particular, nanovoids may result from surface contamination of the substrate, in particular contamination due to the presence of organic contaminants, such as volatile solvents, siloxanes, volatile organic substances, and the like. Control of these types of organic contaminants is important for quality and reproducibility in imprint lithography. As used herein, the term "nanovoid" refers to open voids on the surface of an imprint layer formed on a substrate, the void having saucer-like geometry with a diameter larger than thickness or depth of the void, typically on the order of three or more times larger than the thickness or depth, with typical diameters ranging from 10 nm to 50 µm. The radius of the bottom surface curvature of the nanovoid is also typically much larger than the diameter of the nanovoid. Diameter and thickness or depth of nanovoids may be dependent on thickness or depth of the formed layer, but are typically less than or equal to thickness of the layer. FIG. 3 depicts nanovoid 60 on the surface of formed imprint layer 46, nanovoid 60 having a diameter $d_1$ larger than its thickness $t_3$ and less than thickness $t_4$ of layer 46.

Provided herein are fast, simple and effective methods of detecting substrate contamination levels that rely on the detection of nanovoids. In particular, we have found that by depositing liquid polymerizable material in a periodic drop pattern on the substrate, and using a blank (or featureless) imprint template to form a planar imprint layer, periodic nanovoids may be formed on the layer. That is, nanovoids 60 were found to have a periodic arrangement if a periodic liquid polymer drop pattern was used to form the layer. While not being bound by theory, it is believed that as liquid drops spread, local contaminants are moved with drops and aggregate in areas where the drops coalesce, forming a repeating pattern giving rise to a repeating pattern of nanovoids. Exploitation of this property distinguishes nanovoids from imperfections of substrates themselves, additional coating layers, and the like. Such other imperfections are not arranged in a periodic manner, i.e., they are random, unless the substrate is intentionally made and/or manufactured to have such imperfections. Thus we have found the overall level of substrate contamination can be correlated to the number of periodically occurring nanovoids detected per unit area of the substrate.

Figure 4:
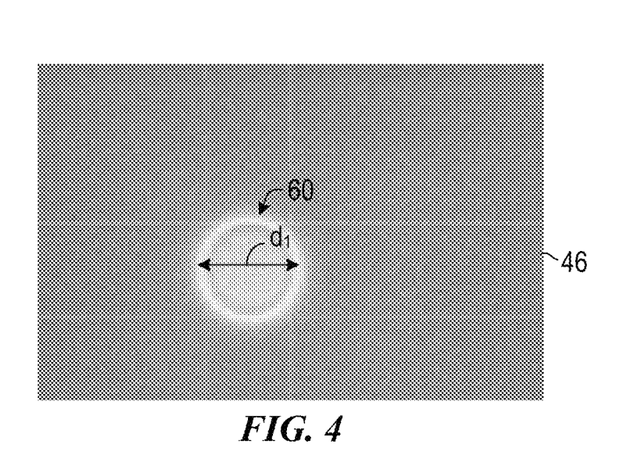
FIG. 4 illustrates a top down view of an image obtained by scanning electron microscopy (SEM) providing an imprinted layer having a nanovoid formed therein.
Figure 5:
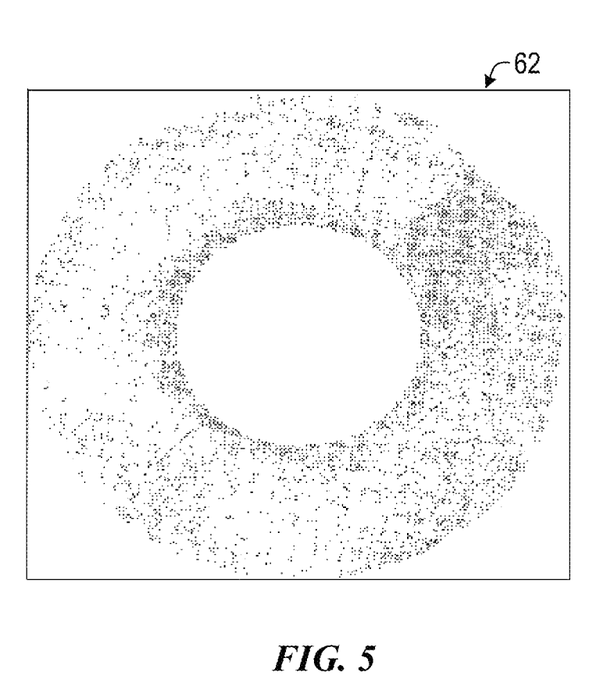
FIG. 5 illustrates a scatter diagram illustrating light scatter defect in an imprinted layer. Scatter defects are illustrated by dark areas.

Nanovoids may be detected and/or analyzed using scanning electron microscopy (SEM) (e.g., image shown in FIG. 4), atomic force microscopy (AFM), and the like. These techniques may be used to directly visualize nanovoids; however, they are slow, costly, and do not always reliably detect nanovoids. Described herein are light scattering systems and techniques for defect analysis having greater precision at faster rates as compared to SEM and AFM. Referring to FIGS. 3-5, generally, a light scattering defect inspection tool may be used to provide a scatter map 62 of the surface of substrate 12 containing nanovoids 60. Light scattering defect inspection tools are known within the industry and commonly used within imprint lithography.

Figure 6:
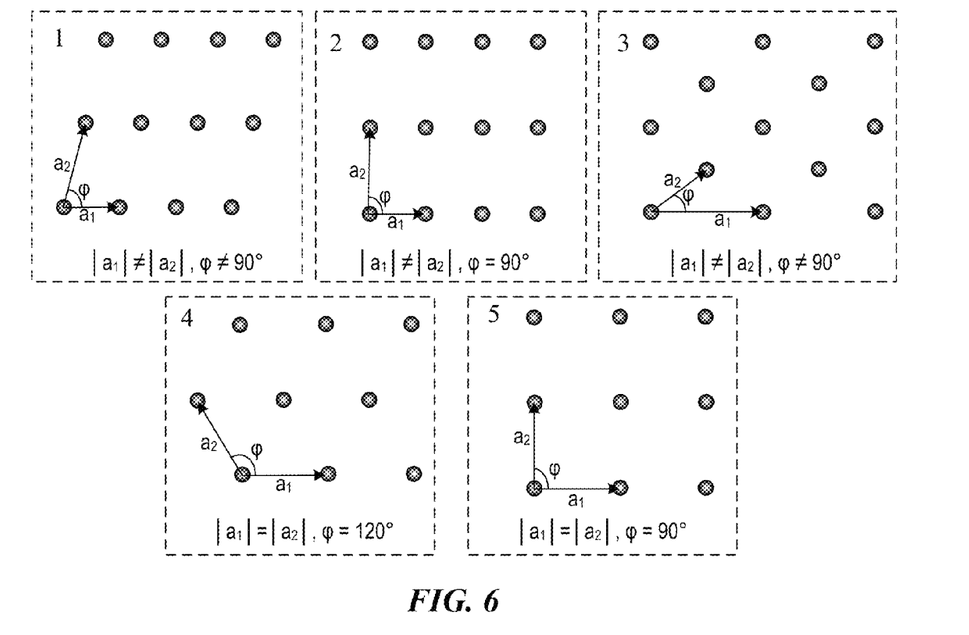
FIG. 6 illustrates exemplary Bravais 2-D lattices (or 2-D space lattices).

A periodic liquid polymer drop pattern may be used to produce formed layer 46 on substrate 12. The liquid polymer drop pattern consists of individual liquid polymer drops placed at predetermined locations on substrate 12. The drop locations may form any of five Bravais 2-D lattices (or 2-D space lattices) as shown in FIG. 6. One example of a periodic drop pattern is a square array of 6 pL drops with period of 170 microns, where $|a_1|=|a_2|$ and $\varphi=90°$. Scatter defects in layer 46 are shown as dark spot within scatter map 62. Some of these defects are nanovoids 60, while others may be imperfections of substrate 12, additional coating layers, and the like.

Figure 7:
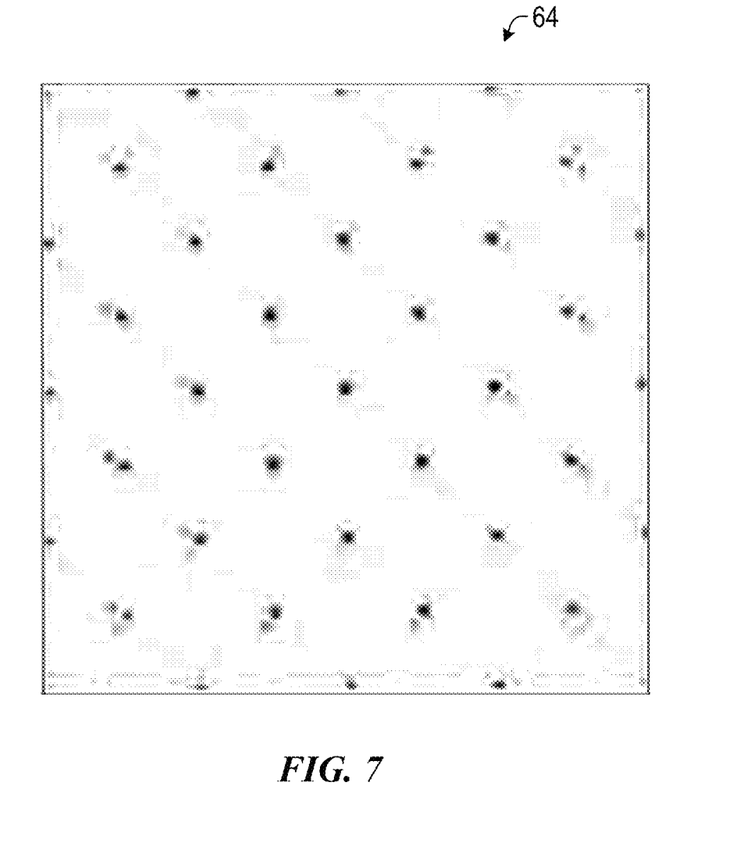
FIG. 7 illustrates Fast 2-D Fourier Transform (FFT) of scatter defects illustrated in FIG. 5.

Referring to FIG. 7, a Fourier transform (FFT) analysis 64 may be provided from the scatter map of the surface of substrates 12 illustrated in FIG. 5. Zero order Fourier component (i.e., peak) is located in the center. The number and symmetry of the Fourier peaks may depend on the symmetry and periodicity of the pattern of nanovoids 60 of FIG. 5. FFT analysis of scatter defects of FIG. 5 may provide a percentage of nanovoids 60 (e.g., 89%) and periodicity of nanovoids (e.g., 4 linear units). Unit values may vary depending on application.

Figure 8:
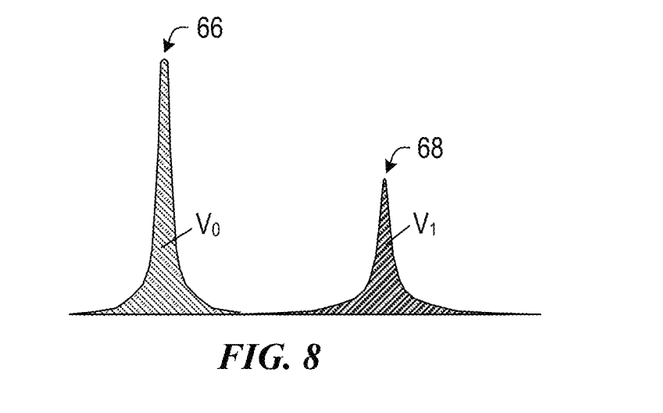
FIG. 8 illustrates schematically zero peak and a first order peak of the FFT graph of scatter defects illustrated in FIG. 5.

Referring to FIG. 8, a volume under FFT peak may be proportional to the number of scatters contributing to the peak. FIG. 8 illustrates schematically volumes $V_0$ and $V_1$ under the zero order peak 66 and first order peak 68 respectively. Scatterers $N_O$, both ordered and non-ordered, may contribute to the zero order peak 66, while only ordered scatterers contribute to the first order peak 68. The ratio $r=V_1/V_0$ distinguishes the part of ordered scatterers from the total. Ordered scatterers include nanovoids 60. As such, measuring the ratio r and calculating the value $N_{NV}=r*N_0$, would give the amount of nanovoids 60.

Figure 9:
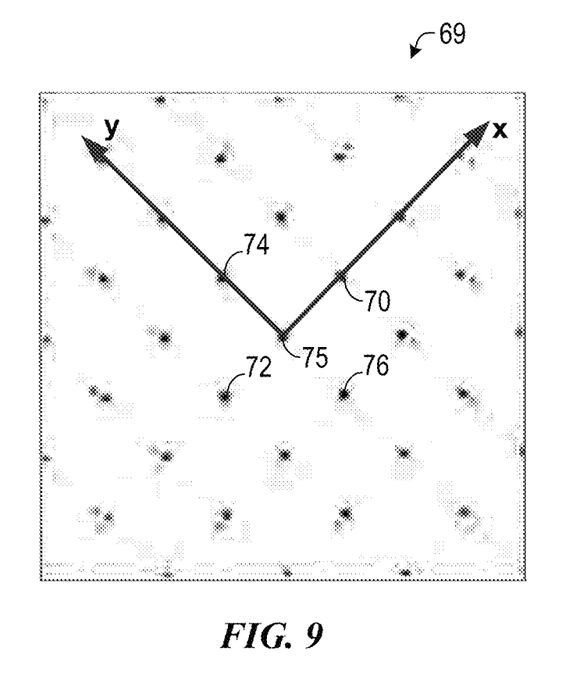
FIG. 9 illustrates the FFT of scatter defects illustrated in FIG. 5 with indexed peaks of first order and zero order for calculating the fraction of ordered scatterers versus total amount of scatterers.

Referring to FIG. 9, for a two dimensional pattern and two-dimensional FFT analysis 69 more peaks may be used instead of one peak. For example two-dimensional FFT analysis 69 of a rectangular pattern (lattice) may include two first order peaks 70 and 72 in a first direction x, and two first order peaks 74 and 76 in a second direction y. The second direction y may be orthogonal to the first direction x. Zero order peak 75 is located in the center. Period in the first direction x may be different than period in the second direction y. In one example, for a square pattern the periods in both directions may be substantially the same. In another example, there may be different amounts of first order peaks (e.g., hexagonal patterns may have 3-axes).

To minimize errors of two-dimensional FFT analysis related to the finite size of the analyzed area and/or spatial resolution, the number of points used for the FFT transform may be averaged. For example, volumes under peaks 70 and 72 may be averaged and/or the volumes under peaks 74 and 76 may be averaged. Thus, ratios in each direction may be represented by:

$$r_x = \frac{(V_{70} + V_{72})}{2V_{75}} \quad \text{(Equation 1)}$$

$$r_y = \frac{(V_{74} + V_{76})}{2V_{75}} \quad \text{(Equation 2)}$$

The larger values of $r_x$ or $r_y$ may be used for calculation of nanovoids 60:

$$N_{NV}=N_0 \cdot \max(r_x, r_y) \quad \text{(Equation 3)}$$

wherein $\max(r_1, r_2 \ldots r_N)$ may be a function giving value substantially equal to maximum value of $r_1, r_2 \ldots r_N$. The number of nanovoids may be provided by:

$$N_{NV}=N_0 \cdot \max(r_1, r_2, \ldots r_i) \quad \text{(Equation 4)}$$

wherein i is the number of symmetry axes for the pattern. For instance, in a hexagonal lattice (pattern) there are three axes (i=3).

As previously discussed in relation to FIGS. 3-4, nanovoids 60 may be caused by surface contamination of substrate 12. Measuring of nanovoids 60 may be used in lieu of or in addition to direct surface analysis techniques such as gas chromatography-mass spectrometry (GC-MS) and time of flight secondary ion mass spectrometry (TOF-SIMS). GC-MS and TOF-SIMS are expensive and take time for results. Using FFT analysis to estimate the level of surface contamination as described herein may be done locally on system 10 of FIG. 1 using light scattering defect tools readily available. FFT analysis is simple, fast and an effective way to provide conclusions on the level of sample surface contamination.

Using the surface contamination detection methods described herein may further provide avenues for improvements in cleanliness of substrates used in imprint lithography. For example, such methods may aid in developing recommendations in nano-imprint lithography for cleaning and coating, storage conditions, sample handling, cleanroom environment, and the like.

Level of contamination may be dependent on prehistory, cleaning procedures, coating, storage conditions of substrate 12, and the like. The nature of contamination, in particular organic contaminants, may be different depending on cleanliness of the environment (e.g., environment within cleanroom), cleanliness of storage containers, and the like. As noted, contamination may include, but is not limited to, organic contaminants such as volatile solvents, siloxanes, volatile organic substances, and the like.

Cleaning and Storage of Substrates

Initially, incoming substrates for use in imprint lithography are typically cleaned using techniques known in the industry and as applicable to the particular substrate (e.g., SC1, UV, Pirinha cleaning, etc.). Cleaning is generally an important step for removing previously accumulated contamination. The pre-history of substrates may impact cleanliness (e.g., where samples were prepared, environment at production site, storage conditions, transportation, and the like). As it may be difficult to require a specified level of cleanliness from distributors, periodic control for different batches of incoming substrates may be performed. For example, levels of contamination of incoming substrates may be measured using the nanovoid detection methods described herein.

Once clean, storage and handling conditions can lead to unacceptable levels of contamination, particularly by organic contaminants, through further preparation, processing and storage. By detecting nanovoids, and thus corresponding levels of contamination, as described herein, optimal preparation steps and storage conditions may be configured. Exemplary substrates were subjected to different preparation steps and storage conditions and the resulting periodic nanovoids were detected and correlated to levels of substrate contamination. Variations in preparation steps and/or storage conditions resulted in detection of nanovoids yielding either satisfactory or unsatisfactory ratings (i.e., acceptable or unacceptable levels of contamination).

Example 1

In a first example, a 65 mm hard drive disk made of glass was cleaned using SC1 process, coated with an approximately 15 nm layer of tantalum, and stored openly in an ambient laboratory environment under HEPA filter for two weeks and then imprinted using a periodic drop pattern of a square array of 6 pL drops with period of 250 microns. A Candela scattering tool was used to determine the scatter defects and generate a scatter map. Fourier transfer (FFT) and ratio analysis were used to determine the total number of periodic nanovoids as previously described above. These particular preparation steps and storage conditions resulted in detection of 47,345 periodic nanovoids over the 30 cm$^2$ area of the disk, or approximately 1,578 nanovoids/cm$^2$, which is an unacceptable level of contamination for this application. An acceptable level would be equal to or less than 23 nanovoids per cm$^2$.

Example 2

In a second example, the substrate was prepared and analyzed as above in Example 1 except that after coating the substrate, the substrate was stored in a clean, sealed storage container and then removed just prior to imprinting. Under these conditions, there were only 58 nanovoids total, or 2 nanovoids/cm$^2$, which was an acceptable level of contamination. These results compared to Example 1 indicate that contamination of the substrates can occur during the storage time between coating and imprinting. In both Examples 1 and 2, the coating process itself was verified to not introduce surface contamination in the coating.

Example 3

In a third example, the substrate was cleaned as above in Example 1 but not coated. As in Example 1, the substrate was stored openly in an ambient laboratory environment under HEPA filter for two weeks. The substrate was then removed, coated, and imprinted, and then analyzed. 8,619 nanovoids were detected, or approximately 287/cm$^2$, an unacceptable level of contamination.

Example 4

In a fourth example, the substrate was cleaned as above in Example 1 but again not coated as in Example 3. The substrate was stored for 5 days in a clean storage container, with steady air flow supplied through a carbon filter. The substrate was then removed, coated and imprinted. Under these conditions, there were only 611 nanovoids, or approximately 20 nanovoids/cm$^2$, which was an acceptable level of contamination.

The above results indicate that undesirable substrate contamination can occur during storage between coating and imprinting. Additionally, contamination may occur during the time between cleaning and coating while substrates are stored, and/or during the time between coating and imprinting during storage. Therefore, to prevent storage contamination, a chemical filter may be used to reduce levels of organic contaminants in the storage environment. Suitable chemical filters are filters capable of removing organic contaminants from air, such as, e.g., carbon filters, liquid nitrogen traps, etc. Even further, storage under a chemical filter (e.g., carbon filter) shows significantly reduced nanovoids as compared to storage only under a HEPA filter.

Cleaning solutions may be configured to reduce substrate surface contamination. Described herein are three such solutions: the cluster tool solution, clean transfer system, and the whole room approach.

Figure 10:
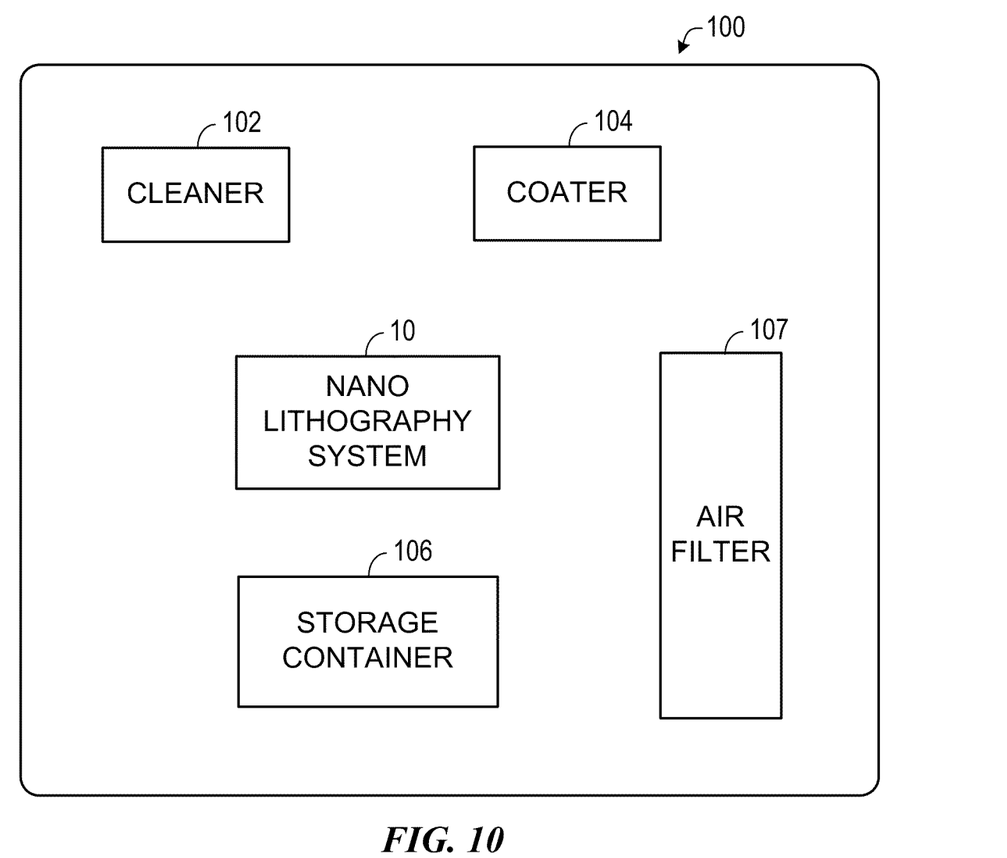
FIG. 10 illustrates a block diagram of an exemplary cluster tool solution for cleaning and/or maintaining cleanliness of a substrate.

Referring to FIG. 10, the cluster tool solution may include a cluster tool 100 having a cleaner 102, a coater 104, system 10, and a storage container 106 within the same airtight enclosed clean environment. Sample handling within cluster tool 100 may vary as long as substrates 12 and cleaner 102, a coater 104, system 10, and storage container 106 are in a substantially clean air environment that is substantially free of contaminants causing nanovoids. An air filter 107 may be used to create the clean air environment. In one example, the air filter may include a chemical filter and a HEPA filter in sequence. The inclusion of a HEPA filter is advantageous in removing particulate matter that may also cause imprint layer defects. Other filters and combinations may also be used as long as they substantially remove the organic contaminants causing nanovoids. Generally, in operation of the cluster tool solution, no contaminated sample carriers and/or sample holders are allowed into cluster tool 100.

Cluster tool 100 may need periodic cleaning and/or routine maintenance for maintenance/repair of elements 10, 102, 104 and/or 106. Characterization of nanovoids may provide a determined threshold of cleanliness for each element 10, 102, 104 and/or 106, in addition to sample handling cassettes, boxes, and the like.

Figure 11:
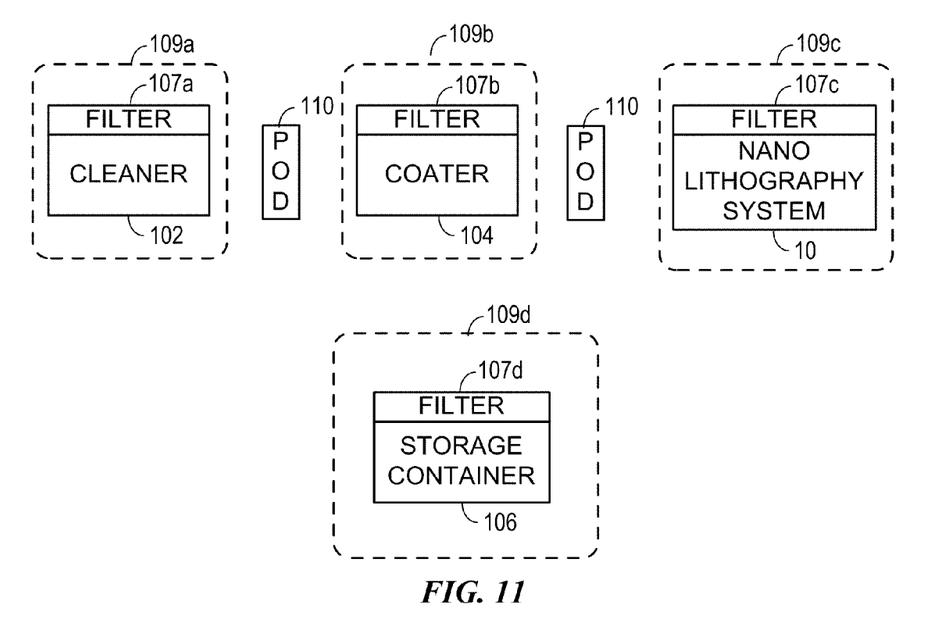
FIG. 11 illustrates a block diagram of an exemplary clean transfer system for cleaning and/or maintaining cleanliness of a substrate.

FIG. 11 illustrates a clean transfer solution. The clean transfer solution uses cleaner 102, coater 104, system 10, and/or storage container 106, each having a separate environment 109a-d and dedicated air control. For example, cleaner 102, coater 104, system 10, and/or storage container 106 may include a separate influx of clean air substantially free of contaminants causing nanovoids. Cleaner 102, coater 104, system 10, and/or storage container 106 may each include a separate combination of filters 107a-d (e.g., chemical filters, HEPA filters, and the like). Any filters and/or combination of filters may be used as long as they substantially remove contaminants causing nanovoids 60.

One or more or portable substrate transfer modules (or pods) 110 may provide transfer of substrates 12 between cleaner 102, coater 104, system 10, and/or storage container 106. Pods 110 may be substantially clean and hermetically sealed. Generally, pods 110 may open and close in such a way that prevents sample contamination from outside environment. It is generally accepted practice in industry that individual environments 109a-d have slightly higher air pressure than that in the cleanroom, i.e. they have positive air pressure compare to the cleanroom. Thus opening a pod inside 109a-d individual environment will prevent influx of contaminants from the cleanroom into the pod space due to positive air pressure difference.

Pods 110 may be periodically cleaned. The efficacy of such cleaning may be monitored by measuring levels of detected periodic nanovoids formed on substrates stored in the pods for a specific period of time. For example, cleaning may be monitored when substrates 12 have been stored in pods for a specific amount of time. Occurrence of nanovoids 60 may be determined for specific intervals of time. Based on occurrence, a maximum time for storage may be configured, with respect to the particular substrate and its application.

A whole room approach can also be provided where cleaner 102, coater 104, system 10, and/or storage container 106 are all within the same clean enclosure along with other additional lab equipment. The whole room approach is different than the cluster approach because there is no limit on presence of other equipment necessary for production (e.g., other lab equipment within the room). As an example, the enclosure may be a manufacturing room and/or a designated area. Clean air substantially free of organic contaminants causing nanovoids may enter the room through a set of filters (e.g., combined chemical/HEPA filters). The amount of filters may depend on size of room and/or other clean room requirements/equipment. No other air may be allowed into room which can be achieved by building slightly positive air pressure compare to outside facility. Again combination of carbon and HEPA filters may be employed, or other filters or combinations of filters may be used as long as they effectively remove organic contaminants causing nanovoids.

Handling and transfer of substrates 12 may be done with substantially clean equipment, containers, and boxes. Incoming handling equipment may be cleaned prior to entry within the room according to ways known in the industry. The effectiveness of the cleaning may be monitored by detecting level of nanovoids found in substrates subjected to the environments of such equipment, according to the methods described herein.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A method for detecting levels of surface contamination of substrates used in imprint lithography, the method comprising the steps of:
   providing a substrate;
   depositing polymerizable material in a periodic drop pattern on the substrate; contacting the polymerizable material with a blank imprint template;
   polymerizing the polymerizable material to form an imprint layer on the substrate;
   detecting the presence of defects on the imprint layer;
   analyzing the detected defects and identifying periodic nanovoid defects within the detected defects; and
   determining the number of periodic nanovoid defects per unit area of substrate, wherein the number of periodic nanovoid defects per unit area correlates to the level of surface contamination of the substrate;
   wherein the detecting step further comprises using light scattering techniques, and further comprising the step of generating a scatter map of the substrate, and wherein the analyzing step further comprises performing a Fourier transform (FFT) analysis of the scatter map.

2. The method of claim 1 wherein the total number of detected defects is determined from the scatter map.

3. The method of claim 1 further comprising determining the ratio of periodic nanovoid defects to total detected defects, wherein the ratio is based on ratio of first and zero peak volumes obtained from the Fourier transform (FFT) analysis.

4. The method of claim 3 wherein the step of determining the number of periodic nanovoid defects further comprises multiplying the ratio of periodic nanovoid defects to total detected defects by the total detected defects.

* * * * *